(12) United States Patent
Braverman et al.

(10) Patent No.: US 6,168,849 B1
(45) Date of Patent: Jan. 2, 2001

(54) MULTILAYER COVER SYSTEM AND METHOD FOR PRODUCING SAME

(75) Inventors: Jaime Braverman, Atlanta; Michael Allen Daley; Arthur Edward Garavaglia, both of Alpharetta; Rebecca Griffin, Woodstock; Tamara Lee Mace, Doraville; David Wayne Primm, Cumming; Eugenio Go Varona, Marietta; Ali Yahiaoui, Roswell, all of GA (US)

(73) Assignee: Kimberly-Clark Worldwide, Inc., Neenah, WI (US)

( * ) Notice: Under 35 U.S.C. 154(b), the term of this patent shall be extended for 0 days.

(21) Appl. No.: 08/968,822

(22) Filed: Nov. 14, 1997

(51) Int. Cl.$^7$ ............................................. B32B 3/10
(52) U.S. Cl. .................. 428/137; 428/138; 428/218; 428/212; 428/913; 442/383; 604/378; 604/383; 156/148; 156/168; 156/176
(58) Field of Search ..................... 428/137, 138, 428/212, 218, 913; 442/381, 382, 383, 392; 604/378, 383; 156/148, 168, 176

(56) References Cited

U.S. PATENT DOCUMENTS

| | | |
|---|---|---|
| 4,397,644 | 8/1983 | Matthews et al. . |
| 4,521,473 | 6/1985 | Sakamoto et al. . |
| 4,758,297 | 7/1988 | Calligarich . |
| 4,886,632 | 12/1989 | Van Iten et al. . |
| 4,935,087 | 6/1990 | Gilman . |
| 4,995,930 | 2/1991 | Merz et al. . |
| 5,207,962 | 5/1993 | Hovis et al. . |
| 5,257,982 | 11/1993 | Cohen et al. . |
| 5,437,653 | 8/1995 | Gilman et al. . |
| 5,458,591 | 10/1995 | Roessler et al. . |
| 5,470,326 | 11/1995 | Dabi et al. . |
| 5,486,166 | 1/1996 | Bishop et al. . |
| 5,490,846 | 2/1996 | Ellis et al. . |
| 5,525,415 | 6/1996 | Quincy, III et al. . |
| 5,531,727 | 7/1996 | Cohen et al. . |
| 5,549,777 | 8/1996 | Langdon et al. . |
| 5,556,392 | 9/1996 | Koczab . |
| 5,573,719 | 11/1996 | Fitting . |
| 5,648,142 | 7/1997 | Phillips . |
| 5,658,639 | 8/1997 | Curro et al. . |
| 5,679,042 | 10/1997 | Varona . |
| 5,932,316 | 8/1999 | Cree et al. . |

FOREIGN PATENT DOCUMENTS

| | | |
|---|---|---|
| 235 309 | 9/1987 | (EP) . |
| 815 819 | 1/1998 | (EP) . |
| 953 324 | 11/1999 | (EP) . |
| 90/14813 | 12/1990 | (WO) . |
| 9311725 | 6/1993 | (WO) . |
| 9428222 | 12/1994 | (WO) . |
| 96/10979 | 4/1996 | (WO) . |
| 96/39109 | 12/1996 | (WO) . |
| 97/23182 | 7/1997 | (WO) . |
| 97/40793 | 11/1997 | (WO) . |
| 98/22068 | 5/1998 | (WO) . |

OTHER PUBLICATIONS

A.A. Burgeni and C. Kapur, Capillary Sorption Equilibria in Fiber Masses, Textile Research Journal, vol. 37, May 1967, pp. 356–366.

*Primary Examiner*—Christopher Raimund
(74) *Attorney, Agent, or Firm*—Pauley Peterson Kinne & Fejer

(57) ABSTRACT

A multilayer material suitable for use as a cover or topsheet for personal care absorbent articles such as diapers, sanitary pads, adult incontinence garments, training pants and the like having a top layer and a bottom, where the top layer forms a plurality of apertures and contacts the bottom layer in land areas disposed between the apertures. The bottom layer has a permeability substantially equivalent to, or higher than, the top layer.

58 Claims, 1 Drawing Sheet

MULTILAYER COVER SYSTEM AND METHOD FOR PRODUCING SAME

BACKGROUND OF THE INVENTION

1. Field of the Invention

This invention relates to a cover material or topsheet for personal care absorbent articles such as diapers, training pants, adult incontinence garments, feminine care products such as sanitary napkins, and the like. The cover material of this invention provides for faster fluid intake rates, lower rewet, less fluid retention, and smaller stain sizes compared to conventional cover materials.

2. Description of Prior Art

Almost all personal care absorbent articles include a cover material, sometimes hereinafter referred to as a liner, topsheet layer, body-side liner, or cover sheet, an absorbent core, and some type of backing material which is generally liquid impervious to help prevent leakage. The types of cover materials generally fall into two main groups based, at least in part, upon performance and aesthetic preferences. In the area of feminine care and sanitary napkins, the market is polarized into two segments, women who prefer clean and dry film covers and women who prefer soft, cloth-like nonwoven covers. The advantage of film covers for sanitary napkins is that they provide a relatively clean and dry surface as menses tends to pass through the film layer and into the interior of the absorbent product. A drawback, however, is that such film layers do not provide the degree of softness and comfort that a nonwoven cover material can provide. An additional drawback is the smooth, slick, non-clothlike feel that is characteristic of many films due. Nonwoven-based cover materials, on the other hand, are very soft and cloth-like in feel, but tend to retain more of the menses at or just below the surface of the cover material which, in turn, makes the product suffer from the standpoint of properties such as cleanliness and dryness. The difference in functionality is a direct result of the structure of nonwoven including small average pore size and nonuniform pore size distribution.

Absorbent articles have typically employed various types of absorbent pads composed of cellulose fibers. Particular absorbent garments have been configured to control the distribution of absorbed liquid. For example, an absorbent article can have a liquid permeable transport layer which is located between a topsheet layer and an absorbent body. In other configurations, a conventional absorbent member can have fluid storage and acquisition zones composed of cellulosic fluff mixed with absorbent gelling particles, and may include a dual-layer absorbent core arrangement comprising a bottom fluff pad containing hydrogel particles, and a top fluff pad with little or no hydrogel particles.

In addition, the absorbent core may consist of synthetic fibers in combination with natural fibers. These types of structures tend to be more resilient and possess a more uniform pore structure under load or when in contact with fluid than traditional absorbents.

Conventional hydrophilic cover materials or topsheets in contact with the skin effectively transport body fluids into the absorbent core, but they cause a wet feel against the skin of the user and may adversely affect skin health. In addition, they may wick liquid in the plane of the layer, allowing liquid to approach the edges of the absorbent article and possibly leak or seep out.

To achieve the goal of softness and a dry feel in topsheets of absorbent articles, many manufacturers have turned to nonwoven fabrics made of hydrophobic fibers for the body-contacting topsheet. While the use of hydrophobic nonwoven fabrics results in improved dry feel, the hydrophobic material hinders wicking into the absorbent core causing fluid to pool on the surface until enough pressure is applied to permeate the structure under conditions of low pressure and flow. As a result, the fluid may run off the pad and leak.

To improve the poor wicking and absorbent properties of hydrophobic materials, it is known to apply a finish comprising surfactants on the surface of the hydrophobic fibers, rendering them wettable or introducing fibers which are intrinsically wettable. Intrinsically wettable fibers may be natural, such as cellulose, or synthetic, such as rayon, polyester, or polyamides. Although providing good intake properties, wettable fibers introduce higher fluid retention and more fluid staining.

In the case of absorbent pads for feminine care, two distinct approaches involving topsheets or covers are commonly employed. One approach is to use a soft, clothlike nonwoven hydrophilic material which increases comfort but has the drawback of fluid retention and staining. A second approach is to use an apertured plastic film of hydrophobic polymer or other materials. The hydrophobic cover material repels many body fluids while the apertures allow wicking away from the cover into the absorbent material below.

Theoretically, the hydrophobic apertured material should allow the user's skin to remain relatively dry while allowing wicking in the z-direction (normal to the plane of the cover) into the underlying absorbent core. However, in practice, hydrophobic apertured films possess a number of problems. Apertured films have the drawback of being disliked by some users for their plastic and hot feel. Likewise, pockets or pools of liquid may form between the film and the user's skin. In the absence of hydraulic pressure or physical compression, menses in particular may pool on the hydrophobic surface rather than penetrate into the apertures, especially if there is a significant interfacial gap between the cover and the underlying absorbent material.

Accordingly, there is a need for an improved cover material which can provide the clean and dry feel characteristic of hydrophobic film cover materials while also delivering the softness of nonwoven cover materials.

SUMMARY OF THE INVENTION

Accordingly, it is one object of this invention to provide a material structure for use as a topsheet or cover in a personal care absorbent article such as a sanitary napkin, catamenial pad, pantiliner, incontinence guard, diapers or training pants for infant care, adult care or child care, bandages, or wound dressings capable of handling viscous or viscoelastic fluids, as well as elastic fluids.

It is another object of this invention to provide a topsheet or cover layer for personal care absorbent articles which is soft and comfortable, absorbent, clean and dry.

These and other objects of this invention are achieved by a multilayer cover system for personal care absorbent articles in accordance with this invention comprising a top layer and a bottom layer, the top layer forming a plurality of top layer apertures which can extend down into and/or through the bottom layer and having land areas between the apertures, the top layer contacting the bottom layer in the land areas, and the bottom layer having a permeability substantially equal to or higher than the top layer. The top layer and the bottom layer comprise at least one material selected from the group consisting of nonwovens, wovens, foams, fibrous structures, and mixtures and combinations thereof and composites of film and nonwovens, wovens, foams and/or fibrous structures. Thus, the approach of this invention is to accept the attributes of softness and comfort that nonwoven covers typically offer and address the issue of poor fluid functionality typical of conventional nonwoven covers. To satisfy these requirements, it is important to understand why these systems have poor fluid functionality and identify opportunities to address these issues.

It is well known in the art that nonwoven webs contain a random arrangement of fibers joined by bonding points that provide the mechanical integrity for these materials. These characteristics have an important influence on fluid management. Due to the random arrangement of fibers, a nonuniform pore size is present through the width and length of a specific web. As a result of this non-uniformity, fluid is retained in the small pores, creating a material which lacks a clean and dry appearance. In addition, the bonding points provide a barrier for the fluid to penetrate the network of the web and, thus, hold the fluid until a force is applied to make the fluid rewet. Part of the novelty of this invention is to provide closer contact of the apertured top layer to a second layer in order to provide the necessary desorption means that allow fluid movement to the absorbent core. This invention relates to, but is not restricted to, the use of a two-layer laminate that is apertured to increase the permeability. In addition, differentials in surface energies, wettability, or surface treatments provide better desorption of viscoelastic fluids from the top layer. Generally, the second layer of material has a larger void volume than the first layer so as to provide rapid intake and reduce rewetting while providing a separation of the fluid, thereby allowing the consumers to perceive a certain distance of the fluid to the top cover, effecting a clean and dry perception.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Figure 1:
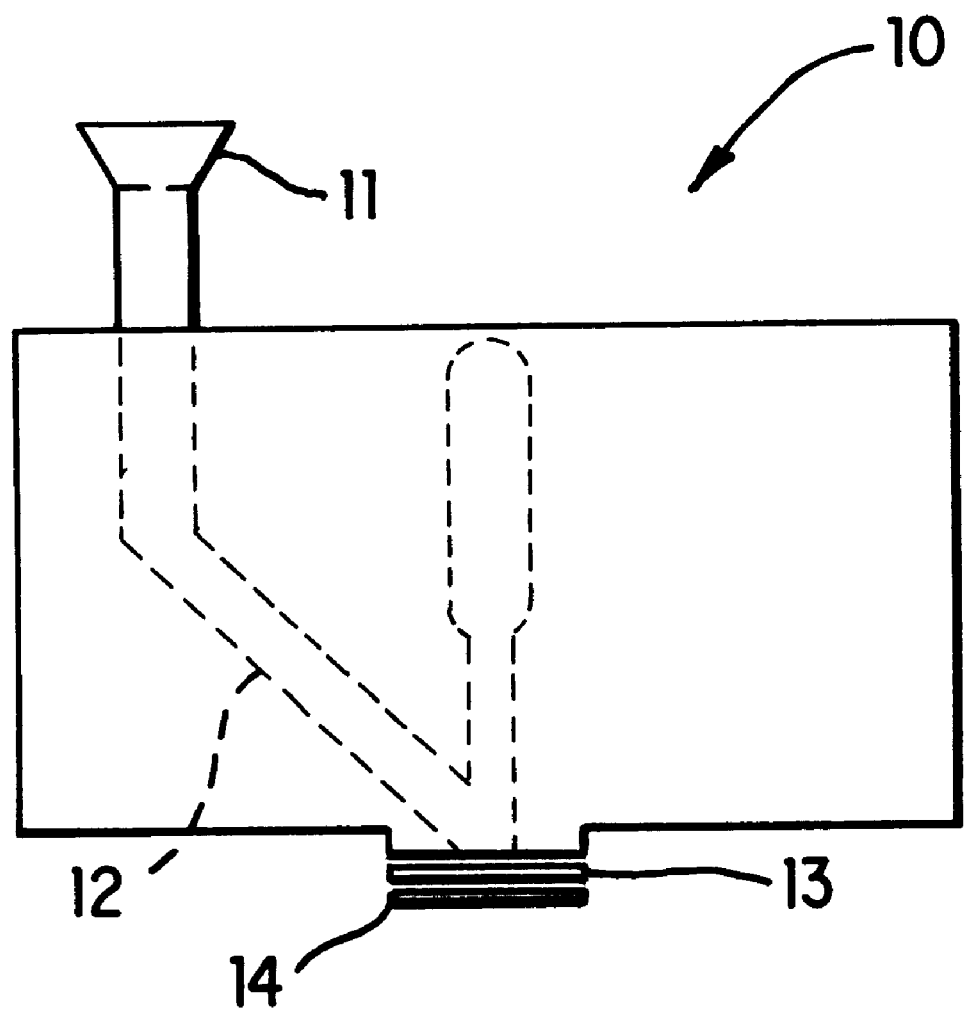
FIG. 1 is a schematic diagram of a rate block apparatus suitable for use in determining fluid intake time of a material or material systems.

This invention relates to a cover or topsheet material for use in personal care absorbent articles which, when utilized in conjunction with an absorbent core, permits superior management of viscous fluids. Proper management of these fluids for feminine care applications, in particular, requires good intake (absorbency), low staining (cleanliness), low rewet (dryness), and low fluid retention (dryness). The material of this invention provides these attributes under a wide range of pressure and flow conditions.

Accordingly, the invention disclosed herein comprises a multilayer composite cover system for personal care absorbent articles comprising a top layer and a bottom layer where the permeability of the top layer is approximately equivalent to or lower than the permeability of the bottom layer. The permeability of the top layer is preferably in the range of about 80 to about 3000 Darcys and the permeability of the bottom layer is preferably in the range of about 1000 to about 28,000 Darcys. The top layer forms a plurality of apertures and comprises land areas between the apertures. The top layer in the land areas contacts the bottom layer. It is important to maintain close contact between the top and bottom layers to provide the necessary pathways for fluid transport to the bottom layer. In addition, the higher permeability of the bottom layer facilitates easy desorption by an absorbent core disposed below the cover/topsheet of the personal care absorbent articles. The top and bottom layers comprise at least one material selected from the group consisting of nonwovens, wovens, foams, fibrous structures, and mixtures and combinations thereof.

In accordance with one preferred embodiment of this invention, apertures extend through the top and bottom layers, thereby increasing the permeability of both material layers. The apertures provide several functions. They create a visually distinctive material which conveys openness, breathability, and utility of function. More importantly, however, they provide passageways for fluid movement through the structure. Apertures also provide void volume to accommodate different volumes of fluid insult and they eliminate fibers, thereby reducing small pores which entrap the fluid. The size, shape and depth of the pores are critical in determining the fluid management characteristics.

For example, increasing the total open area of the cover system by adding more apertures decreases the number of fibrous regions, thus improving intake, reducing staining, and reducing fluid retention. In accordance with one preferred embodiment of this invention, the total open area of the top layer of the cover system formed by said apertures is in the range of about 5% to about 50%. An increase in the aperture size at equivalent open areas, while improving intake, also increases rewetting.

It is also our belief that aperture shape affects fluid management properties. For shapes that are constricted, such as thin rectangles (the limiting case being lines), fluid intake is more difficult than with more open structures, such as circles or squares. The apertures of the cover system of this invention are preferably of the open structure type having a size in the range of about 100 microns to about 3,000 microns across. One must also balance the pore size and open area such that it presents a pleasing visual cue to the consumer while balancing fluid functionality.

The material of this invention includes a number of other variations which enhance performance. These variations include tailoring the structure and surface chemistry properties of the top and bottom layer in synergistic ways so as to improve interactions therebetween to attain superior fluid management. In accordance with one preferred embodiment, the material of this invention is a two-layer composite comprising a top layer and a bottom layer having apertures extending through both layers. Several fundamental parameters are important to the structure of the top layer, including the void volume, pore size, and surface chemistry. Typically, the top layer should have large pores to facilitate fluid transport to the underlying layers. Increasing the permeability of the top layer improves fluid intake and permits fluid transport to the underlying layers. The top layer should also have a low void volume. Because typical nonwovens have nonuniform pore size distribution and small pores, treatment is required in the top layer to permit intake. The treatment type and level must be optimized to insure appropriate wettability for intake at all pressure and flow conditions while balancing the level of fluid retention, rewet, and staining. Alternatively, there are special groups of treatment chemistries which reduce staining. Some of these chemistries include, but are not limited to, polysiloxane polyethers, as discussed in U.S. Pat. No. 5,525,415.

As previously stated, the top layer should have a relatively low void volume. Lower void volume provides rapid fluid transport to the lower layer while minimizing fluid hangup in small pores in these layers. However, the low void volume and large pores of the top layer should be utilized with a material having adequate fluid masking to attain a clean and dry appearance while maintaining suitable mechanical integrity and formation to maintain its structure during use.

The bottom layer of the multilayer cover system of this invention, as previously stated, has a permeability equivalent to or greater than the permeability of the top layer. The high permeability and larger pore sizes of the bottom layer in comparison to the permeability of the absorbent core of the personal care absorbent article permits desorption. As previously stated, in accordance with one preferred embodiment of this invention, the void volume of the bottom layer is larger than the void volume of the top layer to provide sufficient capacity for fluid containment to handle large and small fluid insults. If the void volume of the bottom layer is too low, fluid can pool on the top surface of the cover, thereby providing the potential for runoff or smearing on the top surface of the cover. However, if the void volume is too large, then the opportunity increases for fluid to hang up in the structure and it will not be adequately desorbed by the absorbent layer. In accordance with one preferred embodiment, the top layer has an average void volume in the range of about 0.0625 mL/in$^2$ to about 1.0 mL/in$^2$ and said bottom layer has an average void volume in the range of about 0.3125 mL/in$^2$ to about 4.125 mL/in$^2$.

Yet another requirement of the bottom layer is that it have sufficient wettability for fluid movement. In accordance with one embodiment, the pores of the bottom layer are much larger than the pores of the top layer. As a result, the material directs fluid in the z-direction (into the depth of the material layers) rather than distributes the fluid in the x-y direction (laterally within the material layers). Even though the pores are large, treatment is required to transport fluid through the web and into the absorbent. By rendering the bottom layer more wettable than the top layer, a surface chemistry or surface energy gradient is created which permits the fluid to be more effectively desorbed from the top layer of the composite.

As previously stated, the top layer of the multilayer cover system of this invention forms a plurality of top layer apertures and has land areas disposed between the apertures. The top layer, in the land areas, contacts the bottom layer. The quality of this interface is very important. For example, if the interface is only weakly attached between the materials, then during actual use, the layers may separate, making it impossible for fluid transport across the layers. This can result in a wet top cover and may lead to leakage once the capacity of the top layer has been exceeded. The interface between the material layers may be improved by secondary bonding from physical entanglement or by stronger primary bonding caused by intermixing of the phases of each layer. Alternatively, good contact between the top and bottom layers can also be achieved by chemical and/or physical bonding. Other means of bonding include adhesive bonding, thermal bonding, ultrasonic bonding, or a combination thereof. Bonding can also occur just at the aperture interface between the two layers or also at the fibrous interface. Contact between these two layers is extremely important in both cases. The more contact between the layers in the apertures, the more readily fluid can be transported to the absorbent. Similarly, the better the interface between the top and bottom layers in the fibrous regions, the more easily fluid can be transported from the top to the bottom layer.

Fibrous or fiber-like elements in the aperture can also cause fluid hangup and retention depending upon their size, surface chemistry, and positioning. If the inside of the aperture is more film-like in nature, then fluid will be transported more easily through the structure. It is important, however, to understand that achieving a film-like structure in the aperture may also increase the stiffness of the material, causing it to feel less lofty. In addition, filming of the apertures may cause them to be rough at the aperture opening or rougher when felt from the top of the aperture. However, having a more fibrous structure may also permit more pathways for fluid to pass through the absorbent core if fluid is retained in the fibrous regions.

In accordance with one embodiment of this invention, the top layer comprises a bi-layer structure having a top section and a bottom section. The lop section has a defined pore size, permeability, and void volume and the bottom section is preferably more wettable than the top section. The pore size and permeability of the bottom section are approximately equivalent to or smaller than the pore size of the top section. The void volume of the bottom section may be the same as, less than, or more than the void volume of the top section. The benefit of this type of structure is that it creates a wettability gradient that will draw fluid from the top surface into the materials into the absorbent core. This material structure can be used independently or in combination with the bottom layer and an absorbent core. More than a first and second section can also be utilized where the structure and surface chemistry gradient are built into each section.

In accordance with another embodiment of this invention, the bottom layer of the multilayer cover system comprises a bi-layer structure having a top section and a bottom section. A bottom layer having such a multilayer structure not only transports the fluid, provides separation, and void volume for the fluid but also distributes the fluid. For example, the top section of the bottom layer may have a higher permeability than the top layer, as before, but the structure below it may consist of a second section having lower permeability for distribution of the fluid based upon orientation of the fibers. This structure would permit fluid intake and distribution.

In accordance with one preferred embodiment of this invention, the top layer is a nonwoven web material and the bottom layer is a through air bonded carded web material where the nonwoven web material and the through air bonded carded web material are joined together by a hot pin aperturing process. In accordance with a particularly preferred embodiment, the nonwoven web material is a spunbond and the through air bonded web layer is a surge material. In accordance with another preferred embodiment, the nonwoven web material is a bonded carded web material and the through air bonded carded web layer is a surge material.

The multilayer cover system of this invention is preferably produced by coaperturing of the top and bottom layers. Such coaperturing can be accomplished by a number of processes including a matched roll pin aperturing process or a pattern/anvil roll pin aperturing process.

The matched roll pin aperturing process is widely used to aperture single layer materials. We have used this process to aperture a multilayer structure where the apertures extend through all of the layers of the multilayer cover system. In this process, a low permeability material is unwound on top of a high permeability material and the two materials are then passed over a bowed bar to an aperturing unit and through a nip. The nip consists of a pair of two matched rolls, one male and one female. The male roll is characterized by a series of pins arranged in a specific pattern extending from a roll. The female roll is characterized by a series of holes into which the pins of the male should fit such that the two rolls are mateable. The two rolls are driven with matched gearing to insure registration. The two rolls are heated with electrical heaters. When the materials pass through the nip, they are apertured by a fundamental coining or punching mechanism by which apertures are created through temperature and pressure. After aperturing, the materials are wound onto a roll.

Equipment used for pin aperturing of the multilayer cover system of this invention has two rolls positioned one on top of the other. In one case, the top roll (male roll) comprises plates in which pins having a diameter of 0.081 inches and providing a defined pattern can be fixed. Other patterns can be used consisting of pins of different size and shape. The female roll has holes in its structure in which the pins can fit. The separation on the two rolls can be varied depending upon the material being processed. Temperature is applied to both rolls in order to aid the process. The temperature of the top roll is in the range of 100° F. (23.5° C.) to 500° F. (118° C.). The temperature of the bottom roll is also in the range of 100° F. to 500° F. Material is processed at the rate of about 10 to about 300 feet per minute. Tension is placed onto either the low permeability layer or the high permeability layer using a driven unwind. If tension is placed on the higher permeability material, the material relaxes after aperturing and the high permeability puckers, causing more interfiber contact between layers and creating a soft, cushiony feel to the top sheet. If tension is applied to the low permeability layer, the material will relax after aperturing, creating a soft, cushiony material.

Another process suitable for producing the multilayer cover material of this invention is the pattern/anvil roll aperturing process consisting of four basic steps: (1) unwinding, (2) aperturing, (3) slitting, and (4) winding. For our pilot line process, two materials are placed on driven unwinds. The low permeability material is placed on the first driven unwind while the high permeability material is placed on the second driven unwind. These two materials are then passed over/through several rolls for web handling where the low permeability material is placed on top of the high permeability material. The materials are then passed over a pull roll which controls the speed of entry to the nip. Both materials then pass to an aperturing unit where they are passed through a nip consisting of a heated pattern roll and a heated anvil roll, where apertures are created based on different speeds. Both the pattern roll and the anvil roll are made of steel, although other material constructions can be used. These rolls are heated using an internal oil system, although other means of healing could be employed, such as electrical heaters or infrared lamps. Apertures are created in the composite when the speed of the anvil roll is run faster than the speed of the pattern roll. Presumably, apertures are created because bulk is built into the nip, increasing the residence time and, through the action of shear and heat, the pins are melted into or through one or more layers of the multilayer cover system. The apertures created are based on a pattern roll. Any number of pattern rolls can be used and their pattern would correlate to the aperture pattern in the material. This pattern has profound effects on fluid handling and aesthetically on consumer perception. The apertured composite is then passed through a slitting station where the material is cut to a desired width and lastly wound onto a base roll. Tension can be placed on either the low permeability layer or the high permeability layer using the driven unwind. If tension is placed on the higher permeability material, the material relaxes after aperturing and the high permeability material puckers, causing more interfiber contact between layers and creating a soft, cushiony feel to the top sheet. If tension is applied to the low permeability layer, the material will relax after aperturing, creating a soft, cushioney material.

Definitions

For the purpose of the following examples, several key words and terms used therein have the following definitions:

"Spunbond" refers to a nonwoven web produced by melt spinning fibers. For the examples hereinbelow, the fibers consisted of polypropylene E5D47 with the addition of 8% $TiO_2$ concentrate termed AMPACET 41438. In addition, the web could consist of solid, shaped, hollow, or bicomponent fibers or a combination thereof.

"BCW-Chisso" refers to a lofty nonwoven web created by carding fibers and orienting them into a web. This web is then passed through a through air dryer where it is bonded. The fibers used in this web consist of a bicomponent fiber obtained from Chisso consisting of a 50/50 weight percent sheath core, where the sheath is produced from LLDPE and the core comprises polypropylene. To render it wettable, a surfactant, HR6, was applied to the fiber.

"Spunbond+" refers to a nonwoven web produced by melt spinning. For this material, a 50/50 side-by-side bicomponent fiber was used comprising LLDPE Dow XUS61800.41 and PP Exxon 3445 with the addition of an 8% $TiO_2$ concentrate termed AMPACET 41438.

"Coapertured composite" refers to a composite consisting of a spunbond material on top and a BCW-Chisso material beneath it. These two materials are then apertured to create holes which extend through both layers. An interface is created between these two materials which is represented by light contact and/or entanglement and/or interpenetration and/or bonding. The degree or extent of this depends on specific materials composition and process conditions. The apertures which extend through both layers are represented by a fibrous/film-like structure created through melting and some flow of the fiber.

"Layer" is defined as a material having a singular given composition, structure, and surface chemistry.

"Multilayer structure" is defined as a material or materials of more than one layer wherein gradients of structure, wettability, composition, fiber denier, pore size, pore volume and/or surface chemistry exist between the layers and may be produced in one or more steps.

"Menses simulant" is a material which simulates the viscoelastic and other properties of menses. To prepare the fluid, blood, such as defibrinated swine blood, is separated by centrifugation at 3000 rpm for 30 minutes, although other methods or speeds and times may be used if effective. The plasma is separated and stored separately, the buffy coat removed and discarded and the packed red blood cells stored separately as well. Eggs, such as jumbo chicken eggs, are separated, the yolk and chalazae discarded, and the egg white retained. The egg white is separated into thick and thin portions by straining the white through a 1000 micron nylon mesh for about three minutes, and the thinner portion discarded. Alternative mesh sizes may be used and the time or method may be varied provided the viscosity is at least that required. The thick portion of egg white which was retained on the mesh is collected and drawn into a 60 cc syringe which is then placed on a programmable syringe pump and homogenized by expelling and refilling the contents five times. In our case, the amount of homogenization was controlled by the syringe pump rate of about 100 ml/min, and the tubing inside diameter of about 0.12 inches. After homogenizing, the thick egg white has a viscosity of about 20 centipoise at 150 sec$^{-1}$ and it is then centrifuged to remove debris and air bubbles. After centrifuging, the thick homogenized egg white, which contains ovomucin, is added to a 300 cc FENWAL Transfer pack using a syringe. Then 60 cc of the swine plasma is added to the transfer pack. The transfer pack is clamped, all air bubbles removed, and placed in a Stomacher lab blender where it is blended at normal (or medium) speed for about 2 minutes. The transfer pack is then removed from the blender, 60 cc of swine red blood cells are added, and the contents mixed by hand kneading for about 2 minutes or until the contents appear homogenous. The final mixture has a red blood cell content of about 30 weight percent and generally is at least within the range of 28–32 weight percent for artificial menses. The amount of egg white is about 40 weight percent.

Test Methods

A. Rate Block Intake Test

This test is used to determine the intake time of a known quantity of fluid into a material and/or material system. The test apparatus consists of a rate block 10. A 4"×4" piece of absorbent 14 and cover 13 are die cut. The specific covers are described in the specific examples. The absorbent used for these studies was standard and consisted of a 250 g/m$^2$ airlaid made of 90% Coosa 0054 and 10% HC T-255 binder. The total density for this system was 0.10 g/cc. The cover 13 was placed over the absorbent 14 and the rate block 10 was placed on top of the two materials. 2 mL of a menses simulant was delivered into the test apparatus funnel 11 and a timer started. The fluid moved from the funnel 11 into a capillary 12 where it was delivered to the material or material system. The timer was stopped when all the fluid was absorbed into the material or material system as observed from the chamber in the test apparatus. The intake time for a known quantity of test fluid was recorded for a given material or material system. This value is a measure of a material or material system's absorbency. Typically, 5 to 10 repetitions of this test were performed and average intake time was determined.

B. Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and hence a dryer product. In considering rewet, three properties are important: (1) intake, if the material/system does not have good intake then fluid can rewet, (2) ability of absorbent to hold fluid (the more the absorbent holds onto the fluid the less is available for rewet), and (3) flowback, the more the cover prohibits fluid from coming back through the cover, the lower the rewet. In our case, we are evaluating a cover system where the absorbent is kept constant and, thus, we are only concerned with properties (1) and (3), intake and flowback, respectively.

A 4"×4" piece of absorbent and cover was die cut. The specific covers are described in the specific examples. The absorbent used for these studies was standard and consisted of a 250 g/m$^2$ airlaid made of 90% Coosa 0054 and 10% HC T-255 binder. The total density for this system was 0.10 g/cc. The cover was placed over the absorbent and the rate block was placed on top of the two materials. In this test, 2 mL of menses simulant are insulted into the rate block apparatus and allowed to absorb into a 4"×4" sample of the cover material which is placed on top of a 4"×4" absorbent piece. The fluid is allowed to interact with the system for 1 minute and the rate block rests on top of the materials. The material system, cover and absorbent are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total of 1 psi is applied. The pressure is held fixed for 3 minutes after which the pressure is removed and the blotter paper is weighed. The blotter paper retains any fluid that was transferred to it from the cover/absorbent system. The difference in weight between the original blotter and the blotter after the experiment is known as the "rewet" value. Typically, 5 to 10 repetitions of this test were performed and average rewet was determined.

C. Intake/Staining Test

An intake/staining test has been developed which enables the stain size, intensity, and fluid retention in components to be observed with fluid flow rate and pressure. Menses simulant was used as the test fluid. A 4"×4" piece of absorbent and cover were die cut. The specific covers are described in the specific examples. The absorbent used for these studies was standard and consisted of a 250 g/m$^2$ airlaid made of 90% Coosa 0054 and 10% HC T-255 binder. The total density for this system was 0.10 g/cc. A material system, cover and core measuring 4"×4", was placed underneath an acrylic plate with an ⅛" diameter hole bored into the center. A piece of ⅛" tubing was connected to the hole with a fitting. Menses simulant was delivered to the sample using a syringe pump at a specified rate and for a specified volume. In these experiments, the pump was programmed to deliver a total volume of 1 mL to the samples, where the samples were under pressures of 0 psi (no contact with plate), 0.008 psi, and 0.8 psi. These pressures were applied using a weight which was placed on top of the acrylic plates and distributed evenly. The flow rate of the pump was programmed to deliver at a rate of 1 mL/sec. The stain size for the cover materials was measured manually and the amount of fluid in each component of the system was measured by weight before and after absorption of the fluid. The stain intensity was evaluated qualitatively by comparison of samples. Staining information was recorded using a digital camera and could be further analyzed with image analysis. Typically, 6 repetitions were performed at each pressure and flow rate from which an average was determined. These averages were then used to determine an average for stain size and fluid retention.

D. Permeability Test

Permeability (Darcys) is obtained from a measurement of the resistance to flow of liquid by the material. A liquid of known viscosity is forced through the material of a given thickness at a constant flow rate and the resistance to flow, measured as a pressure drop is monitored. Darcy's Law is used to determine permeability.

Permeability = flow rate × thickness × viscosity/pressure drop

Units:

| | | |
|---|---|---|
| permeability: | cm$^2$ or Darcy | 1 Darcy = 9.87 × 10$^{-9}$cm$^2$ |
| flow rate: | cm/sec | |
| viscosity: | Pascal-sec | |
| pressure drop: | Pascals | |

E. Pore Size Measurements

The pore radius distribution charts shows pore radius in microns in the x-axis and pore volume (volume absorbed in cc of liquid/gram of dry sample at that pore interval) in the y-axis. This is determined by using an apparatus based on the porous plate method first reported by Burgeni and Kapur in the *Textile Research Journal*, Volume 37, pp. 356–366 (1967). The system is a modified version of the porous plate method and consists of a movable Velmex stage interfaced with a programmable stepper motor and an electronic balance controlled by a computer. A control program automatically moves the stage to the desired height, collects data at a specified sampling rate until equilibrium is reached, and then moves to the next calculated height. Controllable parameters of the method include sampling rates, criteria for equilibrium and the number of absorption/desorption cycles.

Data for this analysis were collected using mineral oil in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. This method is described in more detail in U.S. Pat. No. 5,679,042 by Eugenio Go Varona.

F. PEEL

This method describes a protocol to measure the necessary force to pull apart two layers of a composite.

A sample of 6 inches (machine direction)×2 inches is cut on a precision paper cutter. A tensile strength equipment such as an Instron model 1000, 1122 or 113 or a Twin Albert model Intelect II is used to measure force. The equipment must have clamps that measure 1 inch parallel to the direction of load and 3 inches perpendicular direction. The gauge length must be set to 1 inch and the cross head speed to 12 inches/minute. Samples are measured in the machine direction (MD) and the cross direction (CD). The sample is prepared by separating apart from the composite the second layer (about 2 inches) and both materials are clamped to each jaw of the equipment. After starting the equipment, the jaws separate and the load versus distance of separation is recorded. The peak peel load (lbs) is the largest load over a distance of separation from 1 to 7 inches. The average peel load is the average load over a distance of separation from 1 to 7 inches. The testing is performed at a constant temperature of 73+/-F. and a relative humidity of 50+/-2%.

G. Tensile Properties

This procedure measures the strip tensile/energy and elongation of a specimen. Samples are measured in the machine direction (MD) and the cross direction (CD). A sample of 3 inches×6 inches is placed on the pneumatic jaws of an Instron tensile tester with a load cell of 10 pounds, setting up the gage length to 3 inches and a crosshead speed of 12 inches/minute. The sample is placed on the clamps and the equipment is started. The top clamp is lifted by the equipment at the cross head speed until the specimen breaks. The strip tensile peak load (pounds), the maximum load before the specimen ruptures, and the elongation at break (%) (peak strain) are read from the instrument. The modulus is calculated in the typical manner as the slope of the best fitting line on a stress/strain curve as calculated from zero to the proportional limit. The energy is calculated with the following formula:

$$E = R/500 \times LXS$$

where

E=Energy (inch per pound)
R=Integrator reading
L=Full scale load in pounds
S=Crosshead speed (inch/minute)

This is performed at a constant temperature of 73+/-2 F. and a relative humidity of 50+/-2%.

EXAMPLE 1

Three cover materials were created and evaluated to understand the difference between single and multilayer covers. Cover 1 consisted of a 3.2 denier per fiber (dpf), 0.6 ounce per square yard (osy) spunbond with a density of 0.08 g/cc and a permeability of 511 Darcys. This material is typical of the soft, nonwoven covers that are used commercially. Cover 2 consisted of a composite of 3.2 dpf, 0.6 osy spunbond with a density of 0.08 g/cc and a permeability of 511 Darcys which was thermally bonded to a 10 dpf, 0.7 osy BCW-Chisso with a density of 0.0182 g/cc and a permeability of 15,000 Darcys. Cover 3 consisted of a coapertured composite which was produced from a 3.2 dpf, 0.6 osy spunbond with a density of 0.08 g/cc and a permeability of 511 Darcys and a 10 dpf, 0.7 osy BCW-Chisso with a density of 0.0182 g/cc and a permeability of 15,000 Darcys. This composite was apertured to create a material having an open area of 17% and an aperture size of 1650 microns. The spunbond components in Covers 1–3 were topically treated with 0.3% Ahcovel Base N-62 (ICI Surfactants, Wilmington, Del.). The three covers were evaluated with test methods A, B, and C described hereinbelow. The intake time was measured using test method A for each of the covers and is described in Table 1.

TABLE 1

| Intake Time For Covers 1–3 | | |
|---|---|---|
| Code | Average Intake Time(s) | Standard Deviation |
| Cover 1 | 32 | 7 |
| Cover 2 | 24 | 2.5 |
| Cover 3 | 17 | 1.5 |

As shown, the intake time decreased when a multilayer cover system was used as compared to a single layer cover system. Aperturing the cover system through both layers further decreased the intake time compared to bonding the two layers together. The decreased intake time for dual layer composite systems is due to extra void volume that they provide as well as the interface between those systems that produce rapid transport. The coapertured composite system provides lower intake times than the bonded system because the apertures provide void volume and a direct means of transport. Additionally good fiber to fiber contact at the interface insures rapid transport of fluid in nonapertured regions compared to the bonded material. The rewet value was determined for covers 1–3 using test method B. The results are summarized in Table 2.

TABLE 2

| Rewet ForCovers 1–3 | | |
|---|---|---|
| Code | Average Rewet (grams) | Standard Deviation |
| Cover 1 | 0.45 | 0.05 |
| Cover 2 | 0.13 | 0.04 |
| Cover 3 | 0.03 | 0.01 |

It can be seen that the rewet value for the multilayer covers, cover 2 and cover 3, are much lower than that of the single layer cover system. Cover 3 also has a considerably lower rewet value than cover 2.

The stain size was measured for covers 1–3 using test method C. The average stain size for covers 1–3 was calculated based on each of the stain sizes at each pressure. (See Table 3).

TABLE 3

Stain Size (mm$^2$) and Standard Deviations For Covers 1–3
At Specified Pressures at Flow Rate of 1mL/sec.

| Code | 0 psi | 0.008 psi | 0.078 psi | Average |
|---|---|---|---|---|
| Cover 1 | 480 +/− 33 | 1022 +/− 58 | 752 +/− 131 | 751 |
| Cover 2 | 358 +/− 61 | 1375 +/− 294 | 755 +/− 142 | 829 |
| Cover 3 | 426 +/− 89 | 562 +/− 56 | 518 +/− 34 | 502 |

As shown in Table 3, the average stain size for cover 2 was slightly larger than cover 1, presumably due to bonding points which retained fluid. The average slain size for cover 3 was much smaller than either of the other covers. The fluid retention for these covers under the same conditions is shown in Table 4.

TABLE 4

Amount of Fluid Retained (grams) in the Cover
At Specified Pressures for a Flow Rate of 1mL/sec.

| Code | 0 psi | 0.008 psi | 0.078 psi | Average |
|---|---|---|---|---|
| Cover 1 | .03 | .06 | .04 | .043 |
| Cover 2 | .016 | .062 | .05 | .043 |
| Cover 3 | .02 | .023 | .028 | .024 |

The fluid retention has been measured for the entire cover material. The average amount of fluid retained was similar for both covers 1 and 2. Cover 3 had much lower fluid retention than either of the other covers.

EXAMPLE 2

Two cover materials were produced containing two different aperture sizes with approximately equivalent open areas using test methods A, B, and C to understand the role of aperture size on fluid handling for these composites. Cover 3 consisted of a coapertured composite which was produced from a 3.2 dpf, 0.6 osy spunbond with a density of 0.08 g/cc and a 10 dpf, 0.7 osy BCW-Chisso with a density of 0.0182 g/cc. This material was then apertured to create a material having an open area of 17% and an aperture size of 1650 microns. Cover 4 consisted of coapertured composite which was produced from a 3.2 dpf, 0.6 osy spunbond with a density of 0.08 g/cc and a 10 dpf, 0.7 osy BCW-Chisso with a density of 0.0182 g/cc. This material was then apertured to create a material with an open area of 20% and a pore size of 2900 microns. The spunbond layer components in covers 3 and 4 were topically treated with 0.3% Ahcovel Base N-62. As shown in Table 5, the intake time for cover 4 was slightly higher than for cover 3 but the two were about equivalent.

TABLE 5

Intake Time For Covers 3 and 4

| Code | Average Intake Time(s) | Standard Deviation |
|---|---|---|
| Cover 3 | 17 | 1.5 |
| Cover 4 | 18.35 | 1.93 |

TABLE 6

Rewet For Covers 3 and 4

| Code | Average Rewet gram(s) | Standard Deviation |
|---|---|---|
| Cover 3 | .03 | .01 |
| Cover 4 | .198 | .063 |

TABLE 7

Stain Size (mm$^2$) and Standard Deviations For Covers 3 and 4
At Specified Pressures at Flow Rate of 1mL/sec.

| Code | 0 psi | 0.008 psi | 0.078 psi | Average |
|---|---|---|---|---|
| Cover 3 | 426 +/− 89 | 562 +/− 56 | 518 +/− 34 | 502 |
| Cover 4 | 304 +/− 69 | 565 +/− 60 | 363 +/− 107 | 411 |

TABLE 8

Amount of Fluid Retained (grams) in Covers 3 and 4
At Specified Pressures for a Flow Rate of 1mL/sec.

| Code | 0 psi | 0.008 psi | 0.078 psi | Average |
|---|---|---|---|---|
| Cover 3 | .02 | .023 | .028 | .024 |
| Cover 4 | .018 | .03 | .032 | .04 |

The average rewet as shown in Table 6 was higher for cover 4 than cover 3. In Table 7, the stain area is shown for covers 3 and 4. As can be seen, the stain size is larger for cover 3 than cover 4. Additionally, as shown in Table 8, the fluid retention is slightly higher for cover 4 than cover 3. Over the range reported, the larger aperture size in cover 4 compared to cover 3 had little effect on intake time, showed a substantial increase in rewet, a decrease in staining, and an increase in fluid retention.

EXAMPLE 3

Two first layer spunbond materials were evaluated with different pore structures and the same treatment to understand the importance of the structure of the topsheet on absorbency (test A), dryness (test B), and staining and dryness (test C). These materials differed in their structure but were both topically treated with 0.3% Ahcovel Base N-62. Cover 3 consisted of a coapertured composite which was produced from a 3.2 dpf, 0.6 osy spunbond with a density of 0.08 g/cc, a permeability of 511 Darcys (method D) and a 10 dpf, 0.7 osy BCW-Chisso with a density of 0.0182 g/cc and a permeability of 15,000 Darcys (method D). Cover 6 consisted of a top layer comprised of 5 dpf spunbond fibers at a basis weight of 0.4 osy having a density of 0.042 g/cc at a permeability of 1658 Darcys. Both covers 3 and 6 were apertured to an open area of 17% with an aperture diameter of 1650 microns. Lowering the basis weight and increasing the fiber denier of the spunbond (i.e. cover 6 compared to cover 3) increases the average pore size. Intake time was measured using method A. Cover 6 had lower intake time than cover 3. The reduced intake time for cover 6 was due to the increased average pore size as well as the reduction of small pores. Phenomenologically, this result is also explained by the increased permeability of cover 6 compared to cover 3. The average rewet was measured for covers 3 and 6 using method B.

TABLE 9

Intake Time For Covers 3 and 6

| Code | Intake Time(s) | Standard Deviation |
|---|---|---|
| Cover 3 | 17 | 1.5 |
| Cover 6 | 7.8 | 0.63 |

TABLE 10

Rewet For Covers 3 and 6

| Code | Average Rewet (grams) | Standard Deviation |
|---|---|---|
| Cover 3 | .03 | .01 |
| Cover 6 | .05 | .03 |

In Table 10, one notes that the rewet value is low for both covers. The rewet value is lower for cover 3 compared to cover 6 because the larger pore size and higher permeability of the 4.5 dpf, 0.4 osy spunbond cover permits more fluid flowback through the cover. Method C was used to understand fluid retention and staining at three different pressures 0, 0.008, and 0.087 psi at a flow rate of 1 mL/sec. In Table 12, one observes that cover 6 has less fluid retention than cover 3 at lower pressures compared to higher pressures. The average fluid retention was higher for cover 6 than cover 3. From Table 11, the average stain size was similar for both covers 3 and 6 under pressure.

TABLE 11

Stain Size (mm$^2$) and Standard Deviations For Covers 3 and 6
At Specified Pressures at Flow Rate of 1mL/sec.

| Code | 0 psi | 0.008 psi | 0.078 psi | Average |
|---|---|---|---|---|
| Cover 3 | 426 +/- 89 | 562 +/- 56 | 518 +/- 34 | 502 |
| Cover 6 | 370 +/- 39 | 675 +/- 52 | 526 +/- 45 | 524 |

TABLE 12

Amount of Fluid Retained (grams) in Covers 3 and 6
At Specified Pressures for a Flow Rate of 1mL/sec.

| Code | 0 psi | 0.008 psi | 0.078 psi | Average |
|---|---|---|---|---|
| Cover 3 | .02 | .023 | .028 | .024 |
| Cover 6 | .012 | .033 | .04 | .03 |

EXAMPLE 4

Two cover materials were created and evaluated to understand the difference in wettability for the spunbond layer in coapertured composite. Cover 6 consisted of a coapertured composite which was produced from a 4.5 dpf, 0.4 osy spunbond treated topically with 0.3% Ahcovel Base N-62 with a density of 0.042 g/cc and a permeability of 1658 Darcys and a 10 dpf, 0.7 osy BCW-Chisso with a density of 0.0182 g/cc and a permeability of 15,000 Darcys. Cover 7 consisted of a coapertured composite which was produced from a 4.5 dpf, 0.4 osy spunbond with a density of 0.042 g/cc and a permeability of 1658 Darcys treated topically with 1.0% Masil SF-19 (PPG Industries, Inc., Gurnee, Ill.) and a 10 dpf, 0.7 osy BCW-Chisso with a density of 0.0182 g/cc and a permeability of 15,000 Darcys. Both cover 6 and cover 7 were apertured to an open area of 17% with an aperture diameter of 1650 microns. A test was run to evaluate the wettability of model spunbond webs (3.2 dpf, 0.6 osy) treated with 0.3% Ahcovel Base N-62 and 1% Masil SF-19 using ASTM D117-80. As shown in Table 13, the sink time was reduced for treatment of the spunbond with 1.0% Masil SF-19 compared to treatment with 0.3% Ahcovel demonstrating that treatment with Masil SF-19 creates a web that is more wettable than treatment with 0.3% Ahcovel Base N-62.

TABLE 13

| Spunbond Treated With | Sink Time(s) |
|---|---|
| 0.3% Ahcovel | 15.2 |
| 1.0% Masil SF-19 | 1.6 |

Covers 6 and 7 were evaluated with test methods A, B, and C to understand the impact of wettability of the spunbond layer in a coapertured composite on fluid management. The intake time for covers 6 and 7 was evaluated using test method A. The intake time as shown in Table 14 was similar for cover 6 and 7 because of the relative high permeability of the top layer. As the permeability of the top cover decreases from 1650 Darcys toward 511 Darcys, the cover with the higher wettability should have significantly lower intake time than the cover with lower wettability.

TABLE 14

Intake Time For Covers 6 and 7

| Code | Average Intake(s) | Standard Deviation |
|---|---|---|
| Cover 6 | 7.8 | 0.63 |
| Cover 7 | 8.63 | 0.57 |

The rewet value was measured for covers 6 and 7 using test method B. The rewet value as shown in Table 15 was higher for cover 7 compared to cover 6 because the increase in wettability permitted higher fluid flowback.

TABLE 15

Rewet For Covers 6 and 7

| Code | Average Rewet (grams) | Standard Deviation |
|---|---|---|
| Cover 6 | .05 | .03 |
| Cover 7 | .12 | .082 |

Staining and fluid retention were measured for covers 6 and 7 with test method C. The average stain size, as shown in Table 16, was larger for cover 7 as compared to cover 6.

TABLE 16

Stain Size For Covers 6 and 7
At Specified Pressures at Flow Rate of 1 mL/sec.

| Code | 0 psi | 0.008 psi | 0.078 psi | Average |
|---|---|---|---|---|
| Cover 6 | 370 | 675 | 526 | 524 |
| Cover 7 | 576 | 813 | 584 | 658 |

The higher wettability of the spunbond layer in cover 7 resulted in a larger stain size. The fluid retention for covers 6 and 7 are shown in Table 17.

TABLE 17

Fluid Retained in Covers 8 and 9
At Specified Pressures at Flow Rate of 1 mL/sec.

| Code | 0 psi | 0.008 psi | 0.078 psi | Average |
|---|---|---|---|---|
| Cover 6 | .012 | .033 | .04 | .03 |
| Cover 7 | .017 | .03 | .027 | .025 |

The average amount of fluid retained in the cover was similar for cover 6 and cover 7 due to the high permeability of the top layer. At lower top layer permeabilities, a more wettable material should have higher fluid retention than one which is less wettable.

EXAMPLE 5

Two different cover materials were created to understand the impact of incorporating a wettability gradient in the top spunbond material and its effect on fluid handling. Cover 3 consisted of a coaperured composite which was produced from a 3.2 dpf, 0.6 osy spunbond with a density of 0.08 g/cc treated with 0.3% Ahcovel Base N-62 and a 10 dpf, 0.7 osy BCW-Chisso with a density of 0.018 g/cc. Cover 8 consisted of a bilayer spunbond where the top layer consisted of a 0.3 osy, 5 dpf spunbond which was formed on top of a bottom layer composed of a 0.3 osy, 5 dpf spunbond with a density of 0.08 g/cc, where the bottom layer contained an addition of 1% SF-19 and 1% Ahcovel Base N-62 as an internal additive. This bilayer material was treated with 0.3% Ahcovel Base N-62 for the whole web and heated to 240° F. to bloom the internal treatment. Both covers 3 and 8 were apertured to an open area of 17% with an aperture diameter of 1650 microns. Cover 8 had a reduced intake time compared to cover 3 as shown in Table 18. The average rewet, Table 19, was higher for cover 8 than cover 3. As shown in Table 20, the average stain size was similar for covers 3 and 8. The fluid retention, Table 21, was higher for cover 8 than cover 3.

TABLE 18

Intake Time For Covers 3 and 8

| Code | Average Intake Time(s) | Standard Deviation |
|---|---|---|
| Cover 3 | 17 | 1.5 |
| Cover 8 | 7.5 | 1.31 |

TABLE 19

Rewet For Covers 3 and 8

| Code | Average Rewet (grams) | Standard Deviation |
|---|---|---|
| Cover 3 | .03 | .01 |
| Cover 8 | .2 | .06 |

TABLE 20

Stain Size (mm$^2$) and Standard Deviations For Covers 3 and 8
At Specified Pressures at Flow Rate of 1 mL/sec.

| Code | 0 psi | 0.008 psi | 0.078 psi | Average |
|---|---|---|---|---|
| Cover 3 | 426 +/− 89 | 562 +/− 56 | 518 +/− 34 | 502 |
| Cover 8 | 438 +/− 56 | 536 +/− 129 | 570 +/− 65 | 515 |

TABLE 21

Amount of Fluid Retained (grams) in Covers 3 and 8
At Specified Pressures for a Flow Rate of 1 mL/sec.

| Code | 0 psi | 0.008 psi | 0.078 psi | Average |
|---|---|---|---|---|
| Cover 3 | .02 | .023 | .028 | .024 |
| Cover 8 | .032 | .034 | .034 | .033 |

EXAMPLE 6

Two different coapertured materials were investigated with different spunbond top layers to understand the importance of interfacial strength with different polymer compositions and the effect of interfacial properties on fluid management. Cover 3 consisted of a coapertured composite which was produced from a 3.2 dpf, 0.6 osy spunbond with a density of 0.08 g/cc treated with 0.3% Ahcovel Base N-62 and a 10 dpf, 0.7 osy BCW-Chisso with a density of 0.018 g/cc. Cover 9 consisted of a coapertured composite which was produced from a 3.2 dpf 0.6 osy spunbond+ with a density of 0.08 g/cc treated with 0.3% Ahcovel Base N-62 and a 10 dpf, 0.7 osy BCW-Chisso with a density of 0.018 g/cc. Both covers 3 and 9 were apertured to an open area of 17% with an aperture diameter of 1650 microns. As shown in Table 22, the adhesion between the layers of the composite increased markedly for cover 9 compared to cover 3 as determined from PEEL strengths.

TABLE 22

PEEL Strengths For Covers 3 and 9

| Code | PEEL Peak Load CD (lbs) | PEEL Peak Load MD (lbs) | Avg. PEEL Load CD (lbs) | Avg. PEEL Load MD (lbs) |
|---|---|---|---|---|
| Cover 3 | 0.038 | 0.021 | 0.019 | 0.008 |
| Cover 9 | 0.280 | 0.289 | 0.183 | 0.169 |

TABLE 23

Mechanical Properties For Covers 3 and 9

| Code | CD Peak Load | CD Peak Strain (%) | CD Modulus (psi) | MD Peak Load | MD Peak Strain (%) | MD Modulus (psi) |
|---|---|---|---|---|---|---|
| Cover 3 | 1.15 | 40.39 | 170 | 2.82 | 12.83 | 1566 |
| Cover 9 | 3.18 | 88.26 | 178 | 9.79 | 18.76 | 2928 |

Additionally as seen from Table 23, the mechanical properties for the composite increased significantly for cover 9 compared to cover 3. Overall, a stronger interface between layers is seen for cover 9 compared to cover 3, presumably due to more bonding between layers in the apertures and in fibrous regions at the interface. This improved contact at the interface for cover 9 has profound effects on fluid handling properties. For example in Table 24, the intake time is lower for cover 9 than cover 3. The stain size and fluid retention however are higher for cover 9 than cover 3 as shown in Tables 25 and 26. However, these are only marginal differences compared to the difference in intake observed between cover 9 and 3.

TABLE 24

Intake Time For Covers 3 and 9

| Code | Intake Time(s) | Standard Deviation |
|---|---|---|
| Cover 3 | 17 | 1.5 |
| Cover 9 | 7.44 | 1.6 |

TABLE 25

Stain Size (mm$^2$) and Standard Deviations For Covers 3 and 9 At Specified Pressures at Flow Rate of 1 mL/sec.

| Code | 0 psi | 0.008 psi | 0.078 psi | Average |
|---|---|---|---|---|
| Cover 3 | 426 +/− 89 | 562 +/− 56 | 518 +/− 34 | 502 |
| Cover 9 | 452 +/− 50 | 705 +/− 201 | 547 +/− 140 | 568 |

TABLE 26

Amount of Fluid Retained (Grams) in the Cover For Covers 3 and 9 At Specified Pressures for a Flow Rate of 1 mL/sec.

| Code | 0 psi | 0.008 psi | 0.078 psi | Average |
|---|---|---|---|---|
| Cover 3 | .02 | .023 | .028 | .024 |
| Cover 9 | .028 | .046 | .044 | .04 |

We claim:

1. A multilayer material comprising:
a top layer and a bottom layer, said top layer forming a plurality of top layer apertures and having land areas between said apertures, said top layer in said land areas contacting said bottom layer, and said bottom layer having a permeability one of substantially equivalent to and higher than said top layer and a void volume one of substantially equivalent to and greater than said top layer, whereby said permeability of said top layer is in a range of about 3% to about 12% of the permeability of said bottom layer.

2. A multilayer material in accordance with claim 1, wherein said bottom layer has a wettability one of substantially equivalent to and greater than said top layer.

3. A multilayer material in accordance with claim 1, wherein said bottom layer forms a plurality of bottom layer apertures.

4. A multilayer material in accordance with claim 1, wherein said top layer and said bottom layer comprise at least one material selected from the group consisting of nonwovens, wovens, foams, fibrous structures, and mixtures and combinations thereof and a composite of film and nonwovens, film and wovens, film and foams, and film and fibrous structures.

5. A multilayer material in accordance with claim 1, wherein a total area formed by said apertures is in a range of about 5% to about 50% of said top layer.

6. A multilayer material in accordance with claim 1, wherein slid apertures range in size from about 100 microns to about 3000 microns in diameter.

7. A multilayer material in accordance with claim 1, wherein said top layer has an average top layer pore radius of in a top layer range of about 50 microns to about 500 microns and said bottom layer has an average bottom layer pore radius in a range of about 300 microns to about 5000 microns.

8. A multilayer material in accordance with claim 1, wherein a top layer permeability of said top layer is in a top layer range of about 80 to about 3000 Darcys and a bottom layer permeability of said bottom layer is in a bottom layer range of about 1000 to about 28,000 Darcys.

9. A multilayer material in accordance with claim 1, wherein said top layer and said bottom layer are wettable.

10. A multilayer material in accordance with claim 1, wherein said top layer has an average top layer void volume of about 0.0625 mL/in$^2$ to about 1.0 mL/in$^2$ and said bottom layer has an average bottom layer void volume of about 0.3125 mL/in$^2$ to about 4.125 mL/in$^2$.

11. A multilayer material in accordance with claim 1, wherein said top layer comprises a stain reducing treatment.

12. A multilayer material in accordance with claim 1, wherein said top layer comprises a bi-layer structure having a top section and a bottom section.

13. A multilayer material in accordance with claim 12, wherein said bottom section has a higher wettability than said top section.

14. A multilayer material in accordance with claim 12, wherein said top section comprises a stain reducing treatment and said bottom section comprises a high wettability treatment.

15. A multilayer material in accordance with claim 3, wherein said top layer is a nonwoven web material and said bottom layer is a through air bonded carded web material, said nonwoven web material and said through air bonded carded web material joined together by pin aperturing.

16. A multilayer material in accordance with claim 15, wherein said nonwoven web material is a spunbond and said through air bonded carded web layer is a surge material.

17. A multilayer material in accordance with claim 15, wherein an open area formed by said apertures is in a range of about 5% to about 50%.

18. A multilayer material in accordance with claim 15, wherein said nonwoven web material is a bonded carded web material and said through air bonded carded web layer is a surge material.

19. A multilayer material in accordance with claim 1, wherein said top layer and said bottom layer comprise at least one treatment which renders them wettable.

20. A multilayer material in accordance with claim 1, wherein an average fluid intake time is less than about 45 seconds.

21. A multilayer material in accordance with claim 1, wherein an average rewet is less than about 0.15 grams.

22. A multilayer material in accordance with claim 1, wherein an average stain size is less than about 800 mM$^2$.

23. A multilayer material in accordance with claim 1, wherein a machine direction peel value is in a machine direction range of about 0.21 to about 0.61 lbs and a cross direction peel value is in a cross direction range of about 0.021 to about 0.61 lbs.

24. A method for producing a multilayer cover for a personal care absorbent article comprising:

forming a first layer of a material selected from the group consisting of nonwovens, wovens, foams, fibrous structures, and mixtures and combinations thereof and a composite of film and nonwovens, film and wovens, film and foams, and film and fibrous structures, said first layer having an upper surface and a lower surface;

forming a second layer of said material, said second layer having one of a substantially equivalent and lower permeability and one of a substantially equivalent and lower void volume than said first layer, said second layer permeability being in a range of about 3% to about 12% of said first layer permeability;

placing said second layer on said upper surface of said first layer; and forming a plurality of second layer apertures in at least said second layer one of before and after said placing of said second layer.

25. A method in accordance with claim 24 further comprising forming a plurality of first layer apertures in said first layer.

26. A method in accordance with claim 24, wherein said first layer apertures and said second layer apertures are formed simultaneously.

27. A method in accordance with claim 26, wherein said first layer apertures and said second layer apertures are formed by passing said first layer and said second layer simultaneously through a pin aperturing unit.

28. A method in accordance with claim 27, wherein said pins of said pin aperturing unit are heated to a temperature of about 300° F.

29. A method in accordance with claim 24, wherein said first layer is a through air bonded web and said second layer is one of a spunbond web material and a bonded carded web material.

30. A method in accordance with claim 24, wherein said first layer is subjected to tensioning prior to forming said plurality of first layer apertures and is relaxed after forming of said plurality of first layer apertures.

31. A method in accordance with claim 24, wherein said second layer is subjected to tensioning prior to forming said plurality of second layer apertures and is relaxed after forming of said plurality of second layer apertures.

32. A method in accordance with claim 24, wherein a wettability treatment is applied to said first layer.

33. A method in accordance with claim 24, wherein said first layer and said second layer are held together by one of bonding and interpenetration of fibers.

34. A method in accordance with claim 24, wherein said apertures are formed using pattern/anvil roll aperturing wherein the anvil roll speed is faster than the pattern roll speed.

35. A method in accordance with claim 34, wherein said first layer is tensioned prior to forming said plurality of first layer apertures and relaxed after forming of said plurality of first layer apertures.

36. A method in accordance with claim 34, wherein said second layer is tensioned prior to forming said plurality of second layer apertures and relaxed after forming of said plurality of second layer apertures.

37. A personal care absorbent article comprising:

a cover material comprising a top layer and a bottom layer, said top layer forming a plurality of top layer apertures and having land areas between said apertures, said top layer in said land areas contacting said bottom layer, said top layer and said bottom layer comprising at least one material selected from the group consisting of nonwovens, wovens, foams, fibrous structures, and mixtures and combinations thereof and a composite of film and nonwovens, film and wovens, film and foams, and film and fibrous structures, and said bottom layer having one of a substantially equivalent and higher permeability and one of a substantially equivalent and greater void volume than said top layer, said top layer permeability being in a range of about 3% to about 12% of said bottom layer permeability.

38. A personal care absorbent article in accordance with claim 37, wherein said bottom layer forms a plurality of bottom layer apertures.

39. A personal care absorbent article in accordance with claim 37, wherein said bottom layer has one of a substantially equivalent and a higher wettability than said top layer.

40. A personal care absorbent article in accordance with claim 37, wherein an open area formed by said apertures is in a range of about 5% to about 50% of said top layer.

41. A personal care absorbent article in accordance with claim 37, wherein said apertures range in size from about 100 microns to about 3000 microns in diameter.

42. A personal care absorbent article in accordance with claim 37, wherein a top layer permeability of said top layer is in a top layer range of about 80 to about 3000 Darcys and a bottom layer permeability of said bottom layer is in a bottom layer range of about 1000 to about 28,000 Darcys.

43. A personal care absorbent article in accordance with claim 37, wherein said top layer has an average top layer void volume of about 0.0625 mL/in$^2$ to about 1.0 mL/in$^2$ and said bottom layer has an average bottom layer void volume of about 0.3125 mL/in$^2$ to about 4.125 mL/in$^2$.

44. A personal care absorbent article in accordance with claim 37, wherein said top layer comprises a stain reducing treatment.

45. A personal care absorbent article in accordance with claim 37, wherein said top layer is a nonwoven web material and said bottom layer is a through air bonded web material, said nonwoven web material and said through air bonded web material joined together by pin aperturing.

46. A personal care absorbent article in accordance with claim 45, wherein said nonwoven web material is one of a spunbond web and a bonded carded web material and said through air bonded web layer is a surge material.

47. A sanitary pad comprising:

a cover material comprising a top layer and a bottom layer, said top layer forming a plurality of top layer apertures and having land areas between said apertures, said top layer in said land areas contacting said bottom layer, said top layer and said bottom layer comprising at least one material selected from the group consisting of nonwovens, wovens, foams, fibrous structures, and mixtures and combinations thereof and a composite of film and nonwovens, film and wovens, film and foams, and film and fibrous structures, and said bottom layer having one of a substantially equivalent and higher permeability and one of a substantially equivalent and greater void volume than said top layer said top layer permeability being in a range of about 3% to about 12% of said bottom layer permeability.

48. A sanitary pad in accordance with claim 47, wherein said bottom layer forms a plurality of bottom layer apertures.

49. A sanitary pad in accordance with claim 47, wherein said bottom layer has a higher wettability than said top layer.

50. A sanitary pad in accordance with claim 47, wherein an open area formed by said apertures is in a range of about 5% to about 50% of said top layer.

51. A sanitary pad in accordance with claim 47, wherein said apertures range in size from about 80 microns to about 3000 microns in diameter.

52. A diaper comprising:

a cover material comprising a top layer and a bottom layer, said top layer forming a plurality of top layer apertures and having land areas between said apertures, said top layer in said land areas contacting said bottom layer, said top layer and said bottom layer comprising at least one material selected from the group consisting of nonwovens, wovens, foams, fibrous structures, and mixtures and combinations thereof and a composite of film and nonwovens, film and wovens, film and foams, and film and fibrous structures, and said bottom layer having one of a substantially equivalent and higher permeability and one of a substantially equivalent and greater void volume than said top layer, said top layer permeability being in a range of about 3% to about 12% of said bottom layer permeability.

53. A diaper in accordance with claim 52, wherein said bottom layer forms a plurality of bottom layer apertures.

54. A diaper in accordance with claim 52, wherein said bottom layer has a higher wettability than said top layer.

55. A diaper in accordance with claim 52, wherein an open area formed by said apertures is in a range of about 5% to about 50% of said top layer.

56. A diaper in accordance with claim 52, wherein said apertures range in size from about 80 microns to about 3000 microns in diameter.

57. A multilayer material comprising:

a top layer and a bottom layer, said top layer forming a plurality of top layer apertures and having land areas between said apertures, said top layer in said land areas contacting said bottom layer, and said bottom layer having a permeability one of substantially equivalent to and higher than said top layer, a void volume one of substantially equivalent to and greater than said top layer, and a wettability one of substantially equivalent to and greater than said top layer.

58. A multilayer material comprising:

a top layer and a bottom layer, said top layer forming a plurality of top layer apertures and having land areas between said apertures, said top layer in said land areas contacting said bottom layer, and said top layer having a top layer permeability in a range of about 3% to about 12% of a bottom layer permeability.

* * * * *

UNITED STATES PATENT AND TRADEMARK OFFICE
CERTIFICATE OF CORRECTION

PATENT NO.   : 6,168,849 B1
DATED        : January 2, 2001
INVENTOR(S)  : Jaime Braverman et al.

It is certified that error appears in the above-identified patent and that said Letters Patent is hereby corrected as shown below:

<u>Column 7,</u>
Line 20, delete "(23.5ºC.)" and insert -- (37.8ºC.) --;
Lines 20-21, delete "(118ºC.)" and insert -- (260ºC.) --.

Signed and Sealed this

Nineteenth Day of August, 2003

JAMES E. ROGAN
*Director of the United States Patent and Trademark Office*